United States Patent [19]
Slater et al.

[11] Patent Number: 6,069,702
[45] Date of Patent: May 30, 2000

[54] METHOD AND APPARATUS CONFIGURED FOR IDENTIFICATION OF A MATERIAL

[75] Inventors: John M. Slater; Thomas M. Crawford, both of Idaho Falls, Id.

[73] Assignee: Lockheed Martin Idaho Technologies Company

[21] Appl. No.: 09/208,603

[22] Filed: Dec. 8, 1998

[51] Int. Cl.$^7$ .................................................. G01B 11/00
[52] U.S. Cl. ......................... 356/388; 356/448; 356/300; 356/303; 356/320
[58] Field of Search .................................. 356/388, 448, 356/300, 303, 320

[56] References Cited

U.S. PATENT DOCUMENTS

| | | |
|---|---|---|
| 4,201,468 | 5/1980 | Margolis et al. . |
| 4,927,269 | 5/1990 | Keens et al. .............................. 356/346 |

OTHER PUBLICATIONS

Progress With Optical Gas Sensors Using Correlation Spectroscopy, J.P. Dakin, H.O. Edwards, B.H. Weigl, Elsevier Science, S.A., 1995, pp. 87–93.

A New Concept for Open–Path Air Pollution Monitoring, L.H. Taylor, Sensors, Apr. 1995.

Gas Sensors Using Correlation Spectroscopy Compatible With Fibre–Optic Operation, H.O. Edwards and J.P. Dakin, Optoelectronics Research Center, 1993, pp. 9–19.

Near–Infrared Diode Lasers Monitor Molecular Species, David E. Cooper and Ramon U. Martinelli, Laser Focus World, Nov. 1992, 4 pages.

Optical Remote Measurement of Toxic Gases, William B. Grant, Robert H. Kagann and William A. McClenny, Air & Waste Management Association, Jan. 1992, pp. 18–31.

Non–Mechanical Optical Path Switching and Its Application to Dual Beam Spectroscopy Including Gas Filter Correlation Radiometry, Glen W. Sachse and Liang–Guo Wang, NASA Case No. LAR 14588–1–CU, Feb. 11, 1991, 19 pages.

IR Long–Path Photometry: A Remote Sensing Tool for Automobile Emissions, Gary A. Bishop, John R. Starkey, Anne Ihlenfeldt, Walter J. Williams, and Donald H. Stedman, Analytical Chemistry, vol. 61, No. 10, May 15, 1989, 6 pages.

Detection of Organic Vapors With Active and Passive Sensors: A Comparison, Dennis F. Flanigan, Applied Optics, vol. 25, No. 23, Dec. 1986, pp. 4253–4260.

(List continued on next page.)

*Primary Examiner*—Frank G. Font
*Assistant Examiner*—Reginald A. Ratliff
*Attorney, Agent, or Firm*—Wells St. John Roberts Gregory & Matkin

[57] ABSTRACT

The present invention includes an apparatus configured for identification of a material, and methods of identifying a material. One embodiment of the invention provides an apparatus including a first region configured to receive a first sample, the first region being configured to output a first spectrum corresponding to the first sample and responsive to exposure of the first sample to radiation; a modulator configured to modulate the first spectrum according to a first frequency; a second region configured to receive a second sample, the second region being configured to output a second spectrum corresponding to the second sample and responsive to exposure of the second sample to the modulated first spectrum; and a detector configured to detect the second spectrum having a second frequency greater than the first frequency.

55 Claims, 1 Drawing Sheet

OTHER PUBLICATIONS

Electroopic Phase Modulation Gas Correlation Spectroscopy: a Laboratory Demonstration, David M. Rider, J.T. Schofield, J.S. Margosil, and D.J. McCleese, Applied Optics, vol. 25, No. 17, Sep. 1986, pp. 2860–2862.

Spectral Signatures of Chemical Agents and Simulants, Lynn D. Hoffland, Ronald J. Piffath, James B. Bouck, Optical Engineering, vol. 24, No. 6, Nov./Dec. 1985, 3 pages.

Gas Concentration Measurement by Spectral Correlation: Rejection of Interferent Species, Andre Galais, Gerard Fortunato, and Pierre Chavel, Applied Optics, vol. 24, No. 14, Jul. 15, 1985, pp. 2127–2135.

Remote Sensing of Stratospheric and Mesopheric Winds by Gas Correlation Electrooptic Phas–Modulation Spectroscopy, Daniel J. McCleese and Jack S. Margolis, Applied Optics, vol. 22, No. 27, Sep. 1983, pp. 2528–2534.

Carbon Monoxide Mixing Ratio Inference From Gas Radiometer Data, H. Andrew Wallio, Joseph C. Casas, Barbara B. Gormsen, Henry G. Reichle, Jr., and Mary S. Saylor, Applied Optics, vol. 22, No. 5, Mar. 1, 1983, pp. 749–755.

Electro–Optic Phase Modulation Applied to Correlation Spectroscopy, Jack S. Margolis and Daniel J. McCleese, Jet Propulsion Laboratory, Jan. 10–13, 1983, 4 pages.

Gas Cell Correlation Spectrometer: GASPEC, T.V. Ward and H.H. Zwick, Applied Optics, vol. 14, No. 12, May 19, 1975, pp. 2896–2904.

Remote Detection of Gases by Gas Correlation Spectroradiometry, J.S. Margolis, D.J. McCleese, and J.V. Martonchik, Jet propulsion Laboratory, pp. 114–117.

Remote Sensing of Upper Atmospheric Winds, D.J. McCleese and J.S. Margolis, Jet Propulsion Laboratory, 4 pagfes.

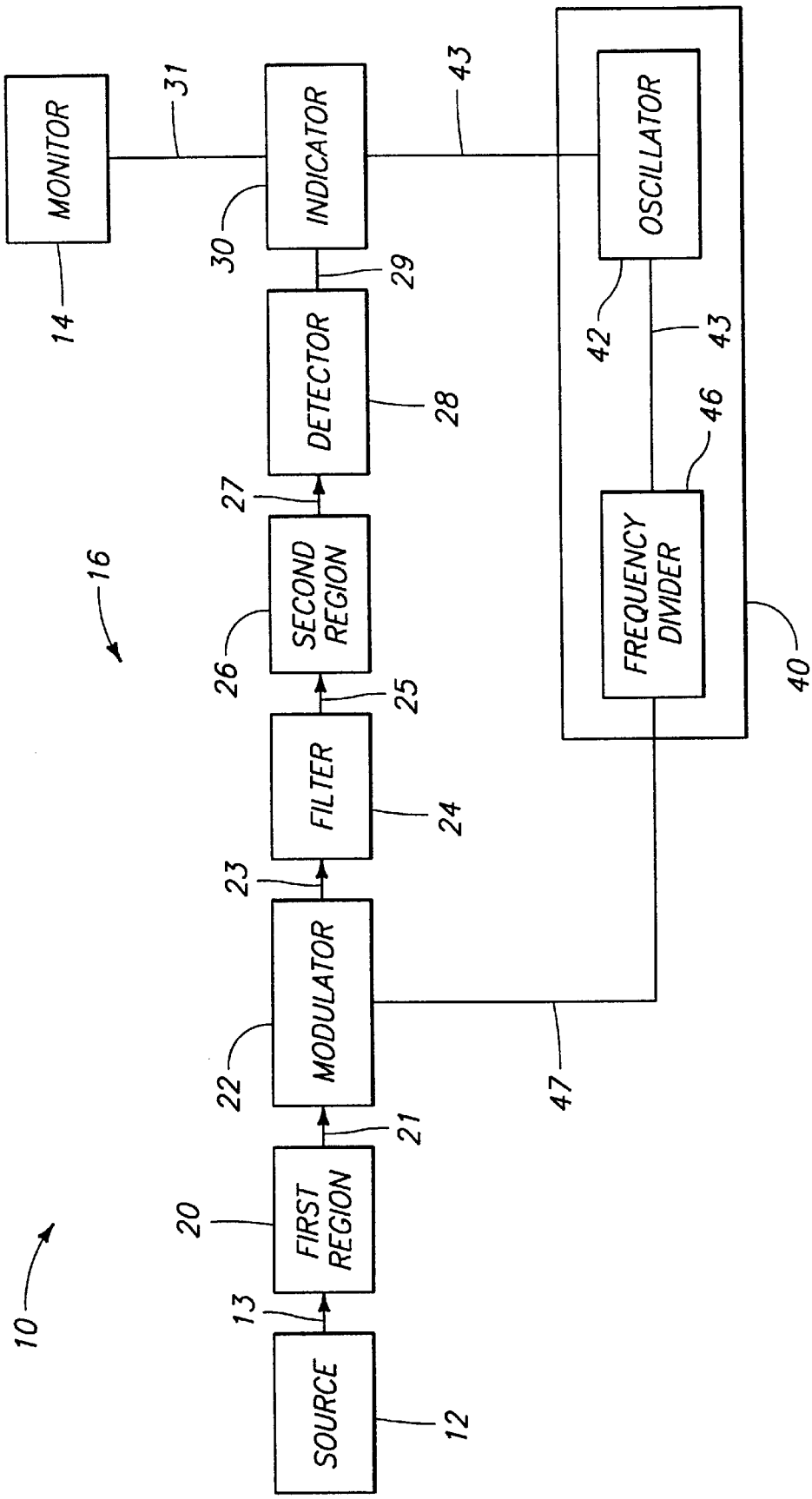

METHOD AND APPARATUS CONFIGURED FOR IDENTIFICATION OF A MATERIAL

CONTRACTUAL ORIGIN OF THE INVENTION

The United States has rights in this invention pursuant to Contract No. DE-AC07-94ID13223 between the U.S. Department of Energy and Lockheed Martin Idaho Technologies Company.

TECHNICAL FIELD

This invention relates to an apparatus configured for identification of a material and methods of identifying a material.

BACKGROUND OF THE INVENTION

Detection devices for identifying chemical species and other materials are known in the art. Spectroscopy has been utilized in detection and identification applications. Conventional material or chemical detection technologies can be classified into general categories.

A first category includes lidar techniques which reflect or scatter a laser beam from a scene. The laser beam is tuned across a spectroscopic absorption feature of the target gas and differential absorption of the returning photons is used for target detection. Because of the complex laser technology utilized to provide appropriate power (e.g., optical parametric generators), these systems are typically built to sense only one or a few compounds. The use of a laser beam precludes use of these techniques in covert applications. A recent development in this technology is the availability of simple laser diodes, however these diodes are minimally tunable and therefore are essentially built to detect single compounds.

Another category comprises open-path FTIR (Fourier transform infrared) spectrometers. Such spectrometers often use a broadband light source in combination with a Fourier transform spectrometer. The weak light sources employed generally require use of a high reflectance mirror if the light source and spectrometer are co-located. These systems have not yet achieved a desirable level of robustness or sensitivity achievable with lidar systems.

Other spectrometry techniques utilize passive infrared. These infrared systems typically use a spectrometer and highly sensitive detector to examine passively occurring emissions or absorption lines. This technique has the benefits of being inherently covert and capable of sensitivities comparable to the active techniques.

These techniques employing conventional spectrometry use dispersive, refractive, or interference-filter based optics. Such spectrometers have the disadvantage of requiring careful calibration to certain wavelength regions in order to admit only the spectral line of interest.

Another detection method includes reference cell spectroscopy or gas filter correlation (GFC) spectroscopy. Conventional reference cell spectroscopy utilizes a reference gas cell on a rotating platform which can be configured to alternately block and unblock incoming light to produce modulation in the output of a downstream detector.

The basic concept is that the degree of intensity modulation due to insertion of a reference cell depends upon whether or not the input spectrum has spectral features that correlate with those of the absorption cell. This conventional technique is severely limited by a host of instrumental problems including the use of multiple optical paths. For example, a lack of balance between the signal and reference optical paths makes it difficult to determine whether a detected "signal" is actually due to the spectral lines of interest or lack of proper calibration or balance of the instrument.

In addition, the modulated signal occurs at the same temporal period as the filter insertion and withdrawal. Therefore, this system cannot separate the desired signal from insertion losses or spurious background effects caused by other conditions (e.g., scattering or reflection losses from the filter windows) because these effects produce modulation at the same frequency as the desired signal.

Therefore, there exists a need to provide improved apparatuses and methods for detecting materials, such as, for example, chemical compounds, which avoid the problems associated with the prior art.

BRIEF DESCRIPTION OF THE DRAWINGS

Preferred embodiments of the invention are described below with reference to the following accompanying drawing.

The FIGURE is a functional block diagram of one embodiment of an apparatus configured to identify a material.

DETAILED DESCRIPTION OF THE PREFERRED EMBODIMENTS

This disclosure of the invention is submitted in furtherance of the constitutional purposes of the U.S. Patent Laws "to promote the progress of science and useful arts" (Article 1, Section 8).

Light passing through a material, such as a chemical species present in a sample, will have certain characteristic wavelengths absorbed or emitted. Radiation or light is preferably passed through two samples provided within plural regions. According to one embodiment, one sample includes a reference or known material and the other sample includes a material to be characterized or detected. For example, one region can comprise a plume of atmospheric air from a monitored environment. The other region can contain a reference material or chemical. The apparatuses and methods of the present invention are configured to identify materials present in the reference region within the plume.

The present invention can be configured to provide indication of materials having spectra over a wide range of frequencies. Preferably, the present invention is configured to detect chemicals having spectra in the infrared, visible, and ultraviolet wavelength regions. The invention is expected to provide a sensitivity enhancement over conventional pulsed detection systems. In addition, apparatuses and methods disclosed herein can be embodied as a passive system.

The apparatuses and methods of the invention utilize modulation of a spectrum of a material to provide detection. The apparatuses and methods utilize the material to be identified as a filter to detect the presence of the same material in the atmosphere or other sample. The present invention performs high resolution spectroscopy without alignment or registration requirements in a preferred embodiment. The invention is preferably configured to sense minute amounts of a material or chemical species in the sample or atmosphere.

Embodiments disclosed herein are configured to wavelength modulate an incoming spectra or light beam by an amount on the order of an absorption or emission bandwidth of typical narrow band materials or chemical species. The preferred apparatuses and methods are configured to provide modulation at microwave frequencies (e.g., one to ten GHz). Such enables sensitivity to the presence of narrow lined (e.g., less than 10 GHz linewidth) materials or chemical species present in a sample, such as atmosphere.

According to a first embodiment of the present invention, an apparatus configured for identification of a material comprises: a first region configured to receive a first sample, the first region being configured to output a first spectrum corresponding to the first sample and responsive to exposure of the first sample to radiation; a modulator configured to modulate the first spectrum according to a first frequency; a second region configured to receive a second sample, the second region being configured to output a second spectrum corresponding to the second sample and responsive to exposure of the second sample to the modulated first spectrum; and a detector configured to detect the second spectrum at a second frequency greater than the first frequency.

A second embodiment of the present invention comprises an apparatus configured for identification of a material within a sample comprising: a source configured to emit radiation; a first region optically coupled with the source and configured to receive a first sample, the first region being configured to output a first spectrum corresponding to the first sample and responsive to exposure of the first sample to the radiation; a signal generator configured to generate a microwave modulation signal having a first frequency and a reference signal having a second frequency approximately twice the first frequency; an optical modulator optically coupled with the first region and configured to receive the modulation signal and modulate the first spectrum according to the first frequency; a second region optically coupled with the optical modulator and configured to receive a second sample and output a second spectrum corresponding to the second sample and responsive to exposure of the second sample to the modulated first spectrum; a detector optically coupled with the second region and configured to detect the second spectrum at the second frequency and output a detection signal at the second frequency responsive to a material being present in the first sample and second sample; and an indicator configured to receive the detection signal and the reference signal, the detection signal and the reference signal individually having the second frequency, the indicator being configured to indicate the presence of the material within the first region and second region.

A method of the present invention for identifying a material comprises: providing a source; providing a first sample; providing a second sample; first exposing the first sample to the source and forming a first spectrum; modulating the first spectrum at a first frequency; second exposing the second sample to the modulated first spectrum and forming a second spectrum; and detecting the second spectrum at a second frequency greater than the first frequency.

Another method of identifying a material comprises: providing a first sample; forming a first spectrum using the first sample; modulating the first spectrum at a first frequency; providing a second sample; forming a second spectrum using the second sample; and detecting the second spectrum at a second frequency greater than the first frequency.

Referring to the FIGURE, an apparatus 10 configured for identifying a material is illustrated. An exemplary material includes a chemical species. The chemical species preferably has a narrow linewidth less than approximately 10 GHz electronic spectra, vibrational spectra, or overtone spectra in the 0.1–10 micron range. Apparatus 10 according to the present invention provides spectroscopic analysis by comparing spectra of samples which may have a common material or chemical species.

The illustrated apparatus 10 comprises a source 12, first region 20, modulator 22, filter 24, second region 26, detector 28, indicator 30, and signal generator 40. In a preferred arrangement, source 12, regions 20, 26, modulator 22, filter 24 and detector 28 are optically coupled in series and define a single optical path 16.

Source 12 is configured to emit radiation 13. An exemplary source 12 includes a broadband light source. Emitted radiation 13 passing through optical path 16 of apparatus 10 is represented by arrows in the FIGURE.

First region 20 and second region 26 are optically coupled with source 12 and configured to receive radiation 13. First region 20 and second region 26 are individually configured to receive a first sample and a second sample, respectively. The first sample and the second sample individually comprise one of a reference material, and a material to be characterized. Some of radiation 13 can be absorbed by the first and second samples. Alternatively, exposed samples can emit respective spectra responsive to exposure to radiation 13.

In one embodiment, the individual one of regions 20, 26 having the reference material comprises a cell. Provision of the reference material within a cell minimizes exposure of the reference to external contamination. Additionally, the other one of regions 20, 26 can receive a plume of atmospheric air, or other media containing the material to be characterized. In monitoring applications it can be preferred to provide access or otherwise expose the individual region 20, 26 having the material to be characterized to the surroundings.

First region 20 is configured to output a first spectrum 21 corresponding to the first sample and responsive to exposure of the first sample to radiation 13. Spectrum 21 can result from absorption of at least some of radiation 13. Alternatively, first spectrum 21 can be formed from emission responsive to exposure of the first sample to radiation 13.

Signal generator 40 of apparatus 10 is configured to provide a reference signal 43 and modulation signal 47. Signals 43, 47 preferably comprise microwave signals. Signal generator 40 includes an oscillator 42 and frequency divider 46 in the depicted embodiment. Oscillator 42 is configured to output a reference signal 43 having a reference frequency. Oscillator 42 comprises a solid state oscillator in one embodiment.

Frequency divider 46 is preferably configured to receive reference signal 43 and lock onto the phase of the frequency of signal 43. Frequency divider 46 is additionally configured to divide the frequency of reference signal 43 by two in the preferred embodiment. Frequency divider 46 is configured to output modulation signal 47 having a first or modulation frequency which is half of a second frequency (i.e., frequency of reference signal 43). Signal generator 40 can be configured to amplify modulation signal 47 prior to application to modulator 22.

In a preferred embodiment, reference signal 43 has a frequency of 1–10 GHz and modulation signal 47 has a corresponding frequency from 0.5–5 GHz. The frequency of reference signal 43 is twice the frequency of modulation signal 47 in the described embodiment.

Modulator 22 of apparatus 10 is optically coupled to first region 20 in the depicted embodiment. In a preferred embodiment, modulator 22 comprises an optical modulator.

Modulator 22 can comprise a crystal phase shifter having an index of refraction dependent upon an applied electric field.

Modulator 22 is configured to receive first spectrum 21 and modulation signal 47. Modulator 22 is preferably configured to modulate first spectrum 21 according to the frequency of modulation signal 47. Varying the electric field applied via modulation signal 47 changes the index of refraction of modulator 22. Modulator 22 is preferably configured to provide a phase shift at peak voltage on the order of one wave or greater. Modulator 22 outputs a modulated first spectrum 23.

Filter 24 preferably comprises an optical prefilter coupled downstream of modulator 22 in optical path 16. Filter 24 is configured to receive modulated first spectrum 23. Filter 24 is configured to partially filter radiation emitted from source 12. In particular, filter 24 comprises a polarizer in one embodiment configured to remove unshifted wavelengths from modulated first spectrum 23. Filter 24 can comprise a dielectric stack prefilter for reducing the noise level within optical path 16. Filter 24 is located at other positions within the optical path 16 in other embodiments. Filter 24 outputs a filtered and modulated first spectrum 25.

Second region 26 is optically coupled via optical path 16 with modulator 22 through filter 24. Second region 26 is configured to receive a second sample comprising either the reference material or the material to be characterized. Second region 26 is configured to output a second spectrum 27 corresponding to the second sample responsive to exposure of the second sample to filtered and modulated first spectrum 25. In embodiments wherein filter 24 is not provided or is alternatively positioned at another location within optical path 16, second region 26 is configured to output second spectrum 27 responsive to exposure of the second sample to modulated first spectrum 23.

Second spectrum 27 is formed from absorption of at least some of the modulated first spectrum 25 in one embodiment. Alternatively, second spectrum 27 is formed from emission responsive to exposure of the second sample to modulated first spectrum 25.

More specifically, second spectrum 27 comprises one of absorption or emission spectrum of the second sample. First spectrum 25 contains a modulated absorption or emission spectrum of the first sample. Modulated first spectrum 25 is passed through second region 26 containing the second sample. Inasmuch as modulator 22 provides frequency shifting of first spectrum 21, a periodic amplitude modulation of the light or radiation of second spectrum 27 results when exposed to modulated first spectrum 25 if the material to be detected is present within both samples. Such results because the incoming absorption (or emission) spectral lines of first spectrum 21 are swept across the spectral lines of second region 26 and the second sample. The temporal period of the amplitude modulation of second spectrum 27 will be half the temporal period of the frequency sweep of the incoming light of first spectrum 25. No modulation of second spectrum 27 occurs if the material to be detected is not present in both the first and second samples of first and second regions 20, 26.

Detector 28 is provided within optical path 16 and optically coupled with second region 26. Detector 28 preferably comprises a fast photovoltaic detector configured for gigahertz bandwidth detection.

In one embodiment, detector 28 comprises an amplitude detector. Detector 28 is configured to detect or receive second spectrum 27 amplitude modulated according to the frequency of reference signal 43. Detector 28 is configured to output a detection signal 29 according to the frequency of the amplitude modulation of second spectrum 27. Detector 28 is configured to output detection signal 29 at the frequency of reference signal 43 responsive to a material being present in the first sample of first region 20 and the second sample of second region 26.

Indicator 30 is coupled with detector 28 and signal generator 40. Indicator 30 is configured to receive reference signal 43 generated within oscillator 42. Further, indicator 30 is configured to receive detection signal 29 from detector 28. Indicator 30 is configured to indicate the presence of a common material within the first and second samples responsive to detection signal 29. Indicator 30 is configured to provide phase sensitive detection of detection signal 29 at the second frequency (i.e., frequency of reference signal 43).

In addition, indicator 30 is configured to indicate the presence of a material responsive to second spectrum 27 being modulated at the second frequency. Indicator 30 is configured to indicate the presence of a material responsive to the frequency of detection signal 29 matching the frequency of reference signal 43. Indicator 30 is configured to indicate the presence of the material within first region 20 and second region 26. In one embodiment, indicator 30 comprises a mixer or lock-in amplifier.

In the depicted embodiment, a monitor 14 is coupled with indicator 30. The indicator is configured to generate an indication signal 31 indicating the presence of a common material or chemical species within the respective samples of first region 20 and second region 26. Monitor 14 can comprise a digital computer or other data gathering device in exemplary embodiments. Alternatively, monitor 14 can comprise an alarm if apparatus 10 is configured to detect harmful or toxic agents.

In compliance with the statute, the invention has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications within the proper scope of the appended claims appropriately interpreted in accordance with the doctrine of equivalents.

We claim:

1. An apparatus configured for identification of a material, the apparatus comprising:
   a first region configured to receive a first sample, the first region being configured to output a first spectrum corresponding to the first sample and responsive to exposure of the first sample to radiation;
   a modulator configured to modulate the first spectrum according to a first frequency;
   a second region configured to receive a second sample, the second region being configured to output a second spectrum corresponding to the second sample and responsive to exposure of the second sample to the modulated first spectrum; and
   a detector configured to detect the second spectrum having a second frequency greater than the first frequency.

2. The apparatus according to claim 1 wherein the modulator comprises an optical modulator.

3. The apparatus according to claim 1 further comprising a source optically coupled with the first region and configured to emit the radiation.

4. The apparatus according to claim 3 further comprising a filter optically coupled with the source and configured to partially filter the radiation.

5. The apparatus according to claim 3 wherein the first spectrum results from absorption of at least some of the radiation.

6. The apparatus according to claim 3 wherein the second spectrum results from absorption of at least some of the modulated first spectrum.

7. The apparatus according to claim 3 wherein the first spectrum is formed from emission responsive to the radiation.

8. The apparatus according to claim 3 wherein the second spectrum is formed from emission responsive to the modulated first spectrum.

9. The apparatus according to claim 1 wherein the detector is configured to detect the second spectrum amplitude modulated according to the second frequency.

10. The apparatus according to claim 1 further comprising a signal generator configured to provide a microwave modulation signal having the first frequency to the modulator.

11. The apparatus according to claim 1 further comprising an indicator coupled with the detector and configured to indicate the presence of a material responsive to the second spectrum being modulated according to the second frequency.

12. The apparatus according to claim 11 wherein the indicator comprises a lock-in amplifier.

13. The apparatus according to claim 11 further comprising a signal generator coupled with the modulator and the indicator, the signal generator being configured to provide a modulation signal having the first frequency to the modulator and a reference signal having the second frequency to the indicator.

14. The apparatus according to claim 13 wherein the second frequency of the reference signal is approximately twice the first frequency of the modulation signal.

15. The apparatus according to claim 1 further comprising an indicator coupled with the detector and configured to indicate the presence of a material responsive to modulation of the second spectrum matching the second frequency.

16. The apparatus according to claim 1 wherein the first and second samples individually comprise one of a reference material and a material that is to be characterized.

17. The apparatus according to claim 16 wherein at least one of the first region and the second region comprise a cell configured to house the reference material.

18. The apparatus according to claim 1 wherein the first region, modulator, second region and detector are optically coupled in series.

19. An apparatus configured for identification of a material within a sample, the apparatus comprising:
  a source configured to emit radiation;
  a first region optically coupled with the source and configured to receive a first sample, the first region being configured to output a first spectrum corresponding to the first sample and responsive to exposure of the first sample to the radiation;
  a signal generator configured to generate a microwave modulation signal having a first frequency and a reference signal having a second frequency approximately twice the first frequency;
  an optical modulator optically coupled with the first region and configured to receive the modulation signal and modulate the first spectrum according to the first frequency;
  a second region optically coupled with the optical modulator and configured to receive a second sample and output a second spectrum corresponding to the second sample and responsive to exposure of the second sample to the modulated first spectrum;
  a detector optically coupled with the second region and configured to detect the second spectrum and output a detection signal having the second frequency responsive to a material being present in the first sample and second sample; and
  an indicator configured to receive the detection signal and the reference signal, the detection signal and the reference signal individually having the second frequency, the indicator being configured to indicate the presence of the material within the first region and second region.

20. A method of identifying a material comprising:
  providing a source;
  providing a first sample;
  providing a second sample;
  first exposing the first sample to the source and forming a first spectrum;
  modulating the first spectrum according to a first frequency;
  second exposing the second sample to the modulated first spectrum and forming a second spectrum; and
  detecting the second spectrum having a second frequency greater than the first frequency.

21. The method according to claim 20 wherein the modulating comprises optically modulating the first spectrum.

22. The method according to claim 20 wherein the modulating comprises modulating using a microwave frequency.

23. The method according to claim 20 further comprising emitting radiation from the source.

24. The method according to claim 23 further comprising emitting the radiation serially through the first sample, second sample and an optical modulator configured to modulate the first spectrum.

25. The method according to claim 23 further comprising filtering the radiation.

26. The method according to claim 23 wherein the forming the first spectrum comprises absorption of at least some of the emitted radiation.

27. The method according to claim 23 wherein the modulated first spectrum comprises radiation and the forming the second spectrum comprises absorption of at least some of the radiation of the modulated first spectrum.

28. The method according to claim 23 wherein the first sample emits the first spectrum responsive to exposure to the radiation.

29. The method according to claim 23 wherein the modulated first spectrum comprises radiation and the second sample emits the second spectrum responsive to exposure to the radiation of the modulated first spectrum.

30. The method according to claim 20 further comprising detecting the second spectrum amplitude modulated according to the second frequency.

31. The method according to claim 20 further comprising indicating the presence of a material within the first sample and the second sample responsive to the detecting.

32. The method according to claim 20 further comprising generating a modulation signal having the first frequency.

33. The method according to claim 32 wherein the modulating comprises using the modulation signal.

34. The method according to claim 20 further comprising generating a detection signal having the second frequency following the detecting.

35. The method according to claim 34 further comprising:
  generating a reference signal having the second frequency approximately twice the first frequency; and indicating the presence of a material within the first sample and second sample responsive to the detection signal and the reference signal.

36. The method according to claim 35 wherein the indicating comprises indicating responsive to the detection signal matching the reference signal.

37. The method according to claim 20 wherein the providings of the first sample and the second sample individually comprise providing one of a reference material and a material that is to be characterized.

38. A method of identifying a material comprising:

providing a first sample;

forming a first spectrum using the first sample;

modulating the first spectrum according to a first frequency;

providing a second sample;

forming a second spectrum using the second sample;

detecting the second spectrum having a second frequency greater than the first frequency.

39. The method according to claim 38 wherein the modulating comprises modulating using a microwave frequency.

40. The method according to claim 38 further comprising exposing the second sample to the modulated first spectrum.

41. The method according to claim 40 wherein the forming the second spectrum is responsive to the exposing.

42. The method according to claim 38 wherein the modulating comprises optically modulating the first spectrum.

43. The method according to claim 38 further comprising emitting radiation from the source.

44. The method according to claim 43 further comprising emitting the radiation serially through the first sample, second sample and an optical modulator configured to modulate the first spectrum.

45. The method according to claim 43 further comprising filtering the radiation.

46. The method according to claim 43 wherein the forming the first spectrum comprises absorption of at least some of the emitted radiation.

47. The method according to claim 43 wherein the modulated first spectrum comprises radiation and the forming the second spectrum comprises absorption of at least some of the radiation of the modulated first spectrum.

48. The method according to claim 43 wherein the first sample emits the first spectrum responsive to exposure to the radiation.

49. The method according to claim 43 wherein the modulated first spectrum comprises radiation and the second sample emits the second spectrum responsive to exposure to the radiation of the modulated first spectrum.

50. The method according to claim 38 further comprising detecting the second spectrum amplitude modulated according to the second frequency.

51. The method according to claim 38 further comprising indicating the presence of a material within the first sample and the second sample responsive to the detecting.

52. The method according to claim 38 further comprising generating a detection signal having the second frequency following the detecting.

53. The method according to claim 52 further comprising:

generating a reference signal having the second frequency approximately twice the first frequency; and indicating the presence of a material within the first sample and second sample responsive to the detection signal and the reference signal.

54. The method according to claim 53 wherein the indicating comprises indicating responsive to the detection signal matching the reference signal.

55. The method according to claim 38 wherein the providings of the first sample and the second sample individually comprise providing one of a reference material and a material that is to be characterized.

* * * * *